United States Patent [19]

Varasi et al.

[11] Patent Number: 5,401,750
[45] Date of Patent: Mar. 28, 1995

[54] DERIVATIVES OF SUBSTITUTED IMIDAZOL-2-ONE AND PROCESS FOR THEIR PREPARATION

[75] Inventors: Mario Varasi, Milan; Franco Heidempergher, Parabiago; Nicola Carfagna, Nerviano; Ruggero Fariello, Luino, all of Italy

[73] Assignee: Farmitalia Carlo Erba S.r.l., Milan, Italy

[21] Appl. No.: 76,153

[22] Filed: Jun. 14, 1993

Related U.S. Application Data

[62] Division of Ser. No. 843,339, Feb. 28, 1992, Pat. No. 5,242,929.

[30] Foreign Application Priority Data

Mar. 27, 1991 [GB] United Kingdom ............... 9106571

[51] Int. Cl.$^6$ .............. C07D 401/04; C07D 451/04; C07D 451/14; A61K 31/46
[52] U.S. Cl. .................................... 514/299; 514/304; 546/112; 546/125
[58] Field of Search ............... 546/125, 126, 112; 514/304

[56] References Cited

U.S. PATENT DOCUMENTS 3,702,327  11/1972  Pengmann ............... 546/19

FOREIGN PATENT DOCUMENTS 0235878  9/1987  European Pat. Off. .
0255297  2/1988  European Pat. Off. .
0323077  7/1989  European Pat. Off. .
0361629  4/1990  European Pat. Off. .

OTHER PUBLICATIONS

Journal of Medicinal Chemistry, vol. 33, No. 7, 1990, pp. 1932–1935.
Journal of Medicinal Chemistry, vol. 34, 1991, pp. 140–151.
Journal of Medicinal Chemistry, vol. 33, No. 6, 1990, pp. 1594–1600.
Derwent Publications Ltd, Abstract of U.S. 3,446,816, American Cyanamid, Issued on May 27, 1969.
Derwent Publications Ltd, Abstract of U.S. 5,600,430, Ely Lilly, Issued on Jul. 15, 1987.
Journal of Medicinal Chemistry, vol. 33, pp. 1929–1932 (1990).
Derwent Publication, Abstract of J6-1033712, Kutobuki Seiyaku KK (2/17/86)
Derwent Publication, Abstract of EP268229, Tanabe Seiyaku KK (5/25/88)

*Primary Examiner*—Alan L. Rotman
*Attorney, Agent, or Firm*—Nikaido, Marmelstein, Murray & Oram

[57] ABSTRACT

Derivatives of 1-phenyl-3-azabicycloalkylimidazolidin-2-ones are provided of general formula (I)

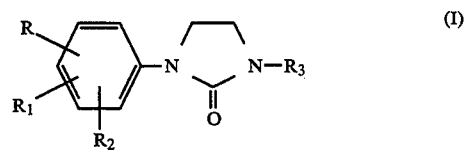

in which inter alia $R_3$ represents a group

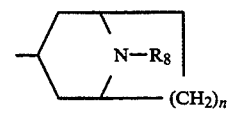

wherein
n is an integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl; and the pharmaceutically acceptable salts thereof, which are useful in the treatment of CNS disorders, gut motility disorders, emesis and migraine, as cognition activators, anti-drug addition agents and analgesic.

4 Claims, No Drawings

DERIVATIVES OF SUBSTITUTED IMIDAZOL-2-ONE AND PROCESS FOR THEIR PREPARATION

This is a division of application Ser. No. 07/843,339, filed Feb. 28, 1992, now U.S. Pat. No. 5,242,929.

The present invention relates to new derivatives of 1-phenyl-3-azabicycloalkyl-imidazolidin-2-ones, to a process for their preparation, to pharmaceutical compositions containing them and to their use as therapeutic agents.

The present invention provides novel compounds having the general formula (I)

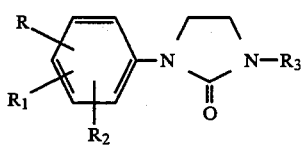

wherein
each of R, $R_1$ and $R_2$, which may be the same or different, is hydrogen, halogen, hydroxy, cyano, C1–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy–carbonyl, nitro, —N($R_4$ $R_5$) in which each of $R_4$ and $R_5$ independently is hydrogen, $C_1$–$C_6$ alkyl, formyl or $C_2$–$C_6$ alkanoyl; or a ($R_6$ $R_7$)N—$SO_2$- group, in which each of $R_6$ and $R_7$ independently is hydrogen or $C_1$–$C_6$ alkyl;
$R_3$ is a group

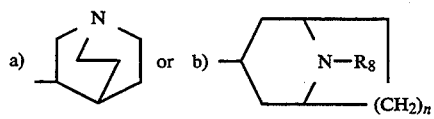

wherein
n is an integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl; and the pharmaceutically acceptable salts thereof.

The formula reported above for the compounds according to the present invention includes all the possible isomers, in particular stereoisomers, as well as their mixtures.

In the compounds of the invention wherein the substituent $R_3$ is a group a), as defined above, such group may be in the R- or S-configuration, or in mixture; thereof.

Similarly when the substituent $R_3$ is a group b), as defined above, such group may be in the endo- or exo- configuration or mixtures thereof, the endo being the preferred.

The invention includes within its scope the metabolites and the metabolic precursors or bio-precursors (otherwise known as pro-drugs) of the compounds of formula (I).

Namely the invention includes compounds which have a different formula to formula (I) above but which nevertheless upon administration to a human being are converted directly or indirectly in vivo into a compound of formula (I).

A halogen atom may be a fluorine, chlorine, bromine or iodine atom, preferably it is chlorine or bromine. The alkyl, alkenyl, alkynyl, alkoxy and alkylthio group may be a branched or straight chain groups.

A $C_1$–$C_6$ alkyl group is preferably a $C_1$–$C_4$ alkyl group, e.g. methyl, ethyl, propyl, isopropyl, butyl, sec. butyl or tert. butyl, in particular methyl or ethyl.

A $C_1$–$C_6$alkoxy group is preferably a $C_1$–$C_4$ alkoxy group e.g. methoxy, ethoxy, propoxy, isopropoxy and butoxy, preferably methoxy and ethoxy.

A $C_1$–$C_6$ alkylthio group is preferably a $C_1$–$C_4$ alkylthio group, e.g. methylthio, ethylthio, propylthio and butylthio, in particular methylthio.

A $C_2$–$C_4$ alkenyl group is preferably allyl.

A $C_2$–$C_4$ alkynyl group is preferably propargyl.

A $C_2$–$C_6$ alkanoyl group is e.g. a $C_2$–$C_4$ alkanoyl group, in particular acetyl and propionyl.

Pharmaceutically acceptable salts of the compounds of formula (I) include acid addition salts, with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, citric, benzoic, cinnamic, mandelic and salicylic acids.

Preferred compounds of the invention are the compounds of formula (I) wherein each of R, $R_1$ and $R_2$, which may be the same or different, is hydrogen, halogen, cyano, $CF_3$, $C_1$–$C_4$ alkylthio, $C_1$–$C_4$ alkoxy or —N($R_4$ $R_5$) in which each of $R_4$ and $R_5$ independently is hydrogen, $C_1$–$C_4$ alkyl, formyl or $C_2$–$C_4$ alkanoyl; $R_3$ is a group

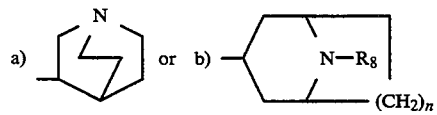

in which n is 1 or 2 and $R_8$ is $C_1$–$C_4$ alkyl; and the pharmaceutically acceptable salts thereof.

Examples of preferred compounds according to the invention are the following:

1-(1-azabicyclo[2.2.2]oct-3 yl)-3-(3-chlorophenyl)- imidazolidin-2-one;

1-(1-azabicyclo[2.2.2]oct-3 yl)-3-(3,5-dichlorophenyl)- imidazolidin-2-one;

1-(1-azabicyclo[2.2.2]oct-3 yl)-3-(3-amino-4-chloro- phenyl)-imidazolidin-2-one;

1-(1-azabicyclo[2.2.2]oct-3 yl)-3-(3-amino-4-chloro- phenyl)-imidazolidin-2-one;

1-(1-azabicyclo[2.2.2]oct-3 yl)-3-(3-bromophenyl)- imidazolidin-2-one;

1-(1-azabicyclo[2.2.2]oct-3 yl)-3-(3-trifluoromethyl- phenyl)-imidazolidin-2-one;

1-(1-azabicyclo[2.2.2]oct-3 yl)-3-phenyl-imidazolidin2- one;

1-(1-azabicyclo[2.2.2]oct-3 yl)-3-(3-methoxyphenyl)- imidazolidin-2-one; and the pharmaceutically acceptable salts thereof, in particular the hydrochloride.

The compounds of the invention and the salts thereof can be obtained by a process comprising reacting a compound of formula (II)

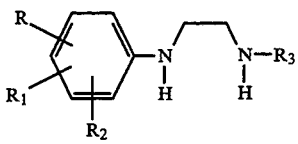

wherein
R, $R_1$, $R_2$ and $R_3$ are as defined above, with a carbonyl containing cyclizing agent and, if desired, converting a compound of formula (I) into another compound of formula (I), and/or, if desired, converting a compound of formula (I) into a pharmaceutically acceptable salt thereof, and/or, if desired, converting a salt into a free-compound, and/or, if desired, separating a mixture of isomers of compounds of formula (I) into the single isomers.

A carbonyl containing cyclizing agent, according to the invention, is e.g. an alkyl-haloformiate, typically a $C_1$-$C_4$ alkyl-haloformiate, in particular methyl chloroformiate, urea or N,N-carbonyldiimidazole, the latter being the preferred.

The cyclizing reaction can be carried out in an aprotic organic solvent chosen for instance from tetrahydrofuran, benzene, toluene and xylene, at reaction temperatures ranging from about 50° C. to reflux temperature and if need be under an inert, e.g. nitrogen, atmosphere.

A compound of formula (I) can be converted, if desired into another compound of formula (I). Thus for instance a compound of formula (I) wherein one or more of R, $R_1$ and $R_2$ is amino can be converted into another compound of formula (I) wherein one or more of R, $R_1$ and $R_2$ is $C_2$-$C_6$ alkanoylamino or formylamino.

A compound of formula (I) in which one or more of R, $R_1$ and $R_2$ is carboxy can be converted into another compound of formula (I) wherein one or more of R, $R_1$ and $R_2$ is $C_1$-$C_6$ alkoxycarbonyl, and vice versa. These optional conversions can be carried out by methods known in themselves.

The optional salification of a compound of formula (I) as well as the conversion of a salt into the free compound and the separation of a mixture of isomers into the single isomers may be carried out by conventional methods.

For example the separation of a mixture of geometric isomers, e.g. endo- and exo-isomers, may be carried out by fractional crystallization from a suitable solvent or by chromatography, either column chromatography or high pressure liquid chromatography.

The compounds of formula (II), which are new, can be obtained by reacting a compound of formula (III)

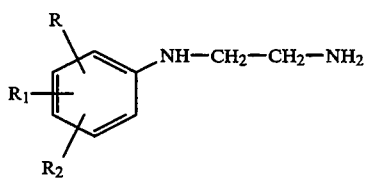

wherein R, $R_1$ and $R_2$ are as defined above, either with a compound of formula (IV) or of formula (V), or a salt thereof in particular the hydrochloride.

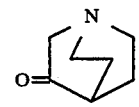

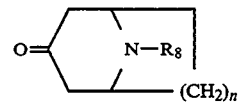

wherein $R_8$ and n are as defined above, thus obtaining a compound of formula (II) wherein $R_3$ is as defined above under a) or b), respectively.

The reaction of a compound of formula (III) with a compound of formula (IV) or (V) can be carried out according to known methods in the art. According to a preferred embodiment of the invention, if the reaction provides a mixture of isomers of a compound of formula (II), before submitting them to the above cyclizing reaction such mixture of isomers can be separated into the single isomers, e.g. endo- and exo-isomers, by methods well known in the art, e.g. by silica gel flash-chromatography. The compounds of formula (III), (IV) and (V) are well known compounds or may be obtained from known compounds and by known methods.

When in the compounds described above groups are present which need to be protected during the reactions described above, such groups can be protected in a conventional way before the reaction takes place and then deprotected. Examples of protecting groups are those employed usually in the chemistry of peptides.

The compounds of the invention are active on the serotoninergic system, in particular as 5HT3 receptor antagonists, as proven for example by the fact that they have been found to be active in antagonizing the von Bezold-Jarisch chemoreflex evoked by 5-HT in the anesthetised rat according to the method described by Fozard J. R., Naunyn-Schmiedeberg's Arch. Pharmacol. 326, 36-44 (1984), The following Table I reports the in vivo 5HT3 antagonist activity data obtained in this test for the representative compound of the invention 1-(1-azabicyclo[2.2.2]oct-3 yl)-3-(3-chlorophenyl)-imidazolidin-2-one (internal code FCE.26778).

TABLE I

Inhibition of the Bezold-Jarisch reflex elicited by 5-HT (20 µg/kg i.v.) by i.v. FCE 26778 in the anesthetized rat.
Values are mean ± S.E.M. from 6 animals

| Compound | Dose (µg/kg i.v.) | % inhibition | $ED_{50}$(µg/kg) (limits) |
|---|---|---|---|
| FCE 26778 | 30 | 26.66 ± 5.25* | |
| | 100 | 59.57 ± 5.87* | 74.94 |
| | 300 | 81.33 ± 3.32* | (54.50–98.39) |
| Vehicle | — | 1.55 ± 4.01 | — |

*p < 0.01 vs controls (Dunnett's test)

The compounds of the invention have also been found to be potent and selective inhibitors of the binding of $^3$H-GR65630 (a selective 5-HT3 receptor antagonist) according to the method described by Kilpatrick G. J. et al., Nature, 330, 746–748 (1987).

The following Table II reports the data obtained in this in vitro test for the representative compound of the invention FCE 26778 in comparison with the known reference compounds MDL 72222 and Metoclopramide.

MDL 72222 is the compound of formula

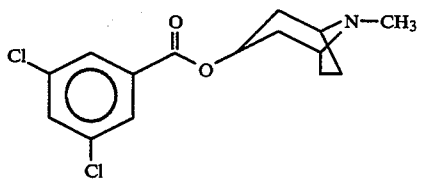

GR 65630 is the compound of formula

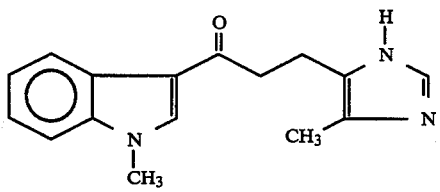

For MDL 72222 see Nature, 330, 746–748 (1987) and for Metoclopramide see Merck Index 10th Edition 6019, page 880.

TABLE II

| 5-HT$_3$ binding affinity[a] for rat entorhinal cortex | | |
|---|---|---|
| Compound | Ki (nM) high | Ki (μM) low |
| FCE 26778 | 4.42 | 1.1 |
| MDL 72222 | 25.5 | — |
| Metoclopramide | 547 | — |

[a][$^3$H]-GR 65630 labelled 5-HT$_3$ sites.

The tested compounds were able to interact with 5-HT$_3$-serotonin receptors labeled in the entorhinal cortex of the rat brain with $^3$H-GR 65630. Of these FCE 26778 interacted according to a two site non-linear fitting model, while MDL 72222 and Metoclopramide displaced 3H-GR 65630 according to one site non-linear fitting: this is the reason why only one (rather than two) Ki value is reported in Table II for the latter two compounds.

The tabulated data clearly show a superior activity of the compounds of the invention over the references. In view of the said activities, the compounds of the present invention can be useful, for example, in the treatment of CNS disorders such as, e.g., anxiety and psychosis, and/or in the treatment of gut motility disorders, and/or emesis.

In view of the above activities the compounds of the invention can be also useful as, for example, anti-migraine or anti-drug addiction agents, or as cognition activators.

The present compounds have further been found to have utility as analgesics. The analgesic activity of the compounds of the invention has been shown, e.g., by the fact that they have proved to be active in the formalin-induced inflammatory pain test described by Dubuisson and Dennis in: "The formalin test: a quantitative study of analgesic effects of morphine, meperidine and brain-stem stimulation in rats and cats" (Pain 4, 161, 1977).

In view of their analgesic properties the compounds of formula (I) can be useful, e.g., in the treatment of pain in mammals, e.g., in the treatment of some forms of inflammatory pain in humans.

The dosage level suitable for administration to adult humans of the compounds of the invention, either for prophylaxis or therapeutic treatment, may range from about 0.010 to about 20 mg/kg of body weight, depending on the chosen route of administration, on the particular compound chosen, on the particular patient under-treatment and also on the nature and severity of the disorder. For instance for the compound of the invention 1-(1-azabicyclo [2.2.2]oct-3-yl)-3-(3-chlorophenyl)-imidazolidin-2-one is suitable administered orally at a dosage in this range.

Preferably the compounds may be, e.g., administered in single or divided doses such that the total daily dosage falls within the range of about 0.020 to about 10 mg/kg per day.

Of course, these dosage regimens may be adjusted to provide the optimal therapeutic response.

The compounds of the invention can be administered in a variety of dosage forms, e.g. orally, in the form of tablets, capsules, sugar, or film coated tablets, liquid solutions or suspensions.

The invention includes pharmaceutical compositions comprising a compound of the invention in association with a pharmaceutically acceptable excipient (which can be a carrier or diluent).

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbares, laurylsulphates; and in general, non-toxic and pharmacologically inactive substances used in pharmaceutical formulations. Said pharmaceutical preparations may be manufactured in known manner, for example by means of mixing granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE 1

N-(1-azabicyclo[2.2.2]oct-3-yl)-N'-(3-chlorophenyl)-1,2-diaminoethane.

To a stirred solution of N-(3-chlorophenyl)-1,2-diaminoethane (1 g; 0.00586 moles) in 25 ml of anhydrous methanol kept under nitrogen atmosphere, 3-quinuclidinone hydrochloride (1.01 g, 0.00627 moles) is added. The pH is adjusted to pH 6 by addition of glacial acetic acid. Sodium cyanoborohydride (0.74 g; 0.0117 moles) is added in two portions. The reaction mixture is refluxed for 10 hours, cooled and then filtered. After evaporation to dryness the residue is taken up with water, basified with 20% sodium hydroxide solution and extracted three times with ethyl acetate. The organic layer is washed with brine, dried over anhydrous sodium sulfate and, after filtration, evaporated to dryness. The residue is purified by silica gel flash-chromatography (methylene chloride-methanol30% ammonium hydroxide, 1.50:50:5 as eluant) to give the desired product as a clear oil (0.66 g).

$C_{15}H_{22}Cl\ N_3$ required=C:64.38; H:7.93; N:15 02; Cl:12.67 found=C:64.64; H:8.02; N:14.81; Cl1:12.27

EXAMPLE 2

N-(endo-8-methyl-8-azabicyclo[3.2.1]oct-3 yl)-N'-(3-chlorophenyl)-1,2-diaminoethane; N-(exo-8-methyl-8-azabicyclo[3.2.1]oct-3 yl)-N'-(3-chlorophenyl)-12-diaminoethane.

To a stirred solution of N-(3-chlorophenyl)-1,2-diaminoethane (2.06 g; 0.01 moles) in 50 ml of anhydrous methanol kept under nitrogen atmosphere, tropinone (1.53 g; 0.011 moles) is added. The pH was adjusted to pH 6 by addition of glacial acetic acid. Sodium cyanoborohydride (1.25 g; 0.02 moles) is added in three portions. The reaction mixture is refluxed 8 hours, cooled and then filtered. After evaporation the residue is taken up with water, basified with 20% sodium hydroxide solution and extracted three times with ethyl acetate. The organic layer is washed with brine, dried over anhydrous sodium sulfate and, after filtration, evaporated to dryness. The residue is purified by silica gel flash-chromatography (methylene chloride-methanol-30% ammonium hydroxide, 150:50:5) as eluant to give 1.2 g of the endo-product as a white solid (m.p. 82.5°-85.5° C.; $C_{16}H_{24}Cl\ N_3$, required=C:65.40; H=8.23; N=14.30, Cl=12.07; found=C=65.06; H:8.04; N=14.19; Cl=12.07) followed by 0.52 g of the exo product as a white solid (m.p. 62°-64° C.; found=C=64.87; H=7.94; N=13.85; Cl=11.81).

EXAMPLE 3

1-(1-azabicyclo[2.2.2]oct-3-yl)-3-(3-chlorophenyl)-imidazolidin-2-one hydrochloride.

To a stirred solution of N-(1-azabicyclo[2.2.2]oct-3 yl)-N'-(3-chlorphenyl)-1,2-diaminoethane (2.7 g; 0.0097 moles) in anhydrous tetrahydrofuran (10 ml), N,N-carbonyldiimidazole(2.04 g; 0.01.25 moles ) is added.

The reaction mixture is refluxed for 8 hours under nitrogen atmosphere. After evaporation, the residue is taken up in ethyl acetate, washed with water and dried over anhydrous sodium sulfate. After filtration and evaporation to dryness, the product is purified by silica gel flash-chromatography (methylene chloride-methanol-30% ammonium hydroxide, 180:20:2 as eluant), followed by treatment with an excess of a solution of hydrochloric acid in ethanol. The crude salt is collected by filtration and recrystallized from absolute ethanol to yield 1.5 g of the desired product; m.p. 234°-239° C.

By proceeding analogously the following compounds can be prepared either as a free product or as a hydrochloride salt thereof.

1-(1-azabicyclo[2.2.2]oct-3-yl)-3-(5-chloro-2-methoxyphenyl)-imidazolidin-2-one hydrochloride m.p. 209°-215° C.;

1-(1-azabicyclo[2.2.2]oct-3-yl)-3-(5-chloro-2-hydroxyphenyl)-imidazolidin-2-one m.p. 164°-167° C.;

(endo)-1-(8-methyl-8-azabicyclo[3.2.1]oct-3-yl)-3-(3-chlorophenyl)-imidazolidin-2-one hydrochloride m.p. 264°-268° C.;

(exo)-1-(8-methyl-8-azabicyclo[3.2.1]oct-3-yl)-3-(3-chlorophenyl)-imidazolidin-2-one hydrochloride hydrate m.p. 239°-243° C.;

(endo)-1-(9-methyl-9-azabicyclo[3.3.1]non-3-yl)-3-(3-chlorophenyl)-imidazolidin-2-one hydrochloride m.p. 243°-249° C.;

(exo)-1-(9-methyl-9-azabicyclo[3.3.1]non-3-yl)-3-(3-chlorophenyl)-imidazolidin-2-one m.p, 157.5°-161.5° C.;

(endo)-1-(8-methyl-8-azabicyclo[3.2.1oct-3-yl)-3-(5-chloro-2-methoxyphenyl)-imidazolidin-2-one hydrochloride m.p. 224°-228° C.;

(endo )-1-(9-methyl-9-azabicyclo[3.3.]non-3-yl)-3-(5-chloro-2-methoxyphenyl)-imidazolidin-2-one hydrochloride m.p. 100° C.;

1-(1-azabicyclo[2.2.2]oct-3-yl)-3-phenyl-1-imidazolidin-2-one m.p. 140°-143° C.;

1-(1-azabicyclo[2.2.2]oct-3-yl)-3-(3,5-dichlorophenyl)-imidazolidin-2-one hydrochloride m.p. 248.5°-254° C.;

1-(1-azabicyclo[2.2.2]oct-3-yl)-3-(3-trifluoromethylphenyl-imidazolidin-2-one m.p. 130.5°-134.5° C.;

1-(1-azabicyclo[2.2.2]oct-3-yl)-3-(3-methylthiophenyl)-imidazolidin-2-one hydrochloride m.p. 205° C. dec.;

1-(1-azabicyclo[2.2.2]oct-3-yl)-3-(4-amino-3-chlorophenyl)-imidazolidin-2-one m.p. 176.5°-182° C.;

1-(1-azabicyclo[2.2.2]oct-3-yl)-3-(4-chlorophenyl)-imidazolidin-2-one m.p. 175°-178° C.;

1-(1-azabicyclo[2.2.2]oct-3-yl)-3-(3-methoxyphenyl)-imidazolidin-2-one m.p. 120°-133° C.;

1-(1-azabicyclo[2.2.2]oct-3-yl)-3-(3-bromophenyl)-imidazolidin-2-one m.p. 132°-136° C.;

1-(1-azabicyclo[2.2.2]oct-3-yl)-3-(3-cyanophenyl)-imidazolidin-2-one m.p. 168°-167° C.;

1-(1-azabicyclo[2.2.2]oct-3-yl)-3-(3-nitrophenyl)-imidazolidin-2-one hydrochloride m.p. 220° C. dec.;

1-(1-azabicyclo[2.2.2]oct-3-yl)-3-(3-methylphenyl)-imidazolidin-2-one m.p. 122°-126° C.;

1-(1-azabicyclo[2.2.2]oct-3-yl-3-(3-amino-4-chlorophenyl)-imidazolidin-2-one m.p. 150°-165° C.;

1-(1-azabicyclo[2.2.2]oct-3-yl)-3-(4-chloro-3-nitro-phenyl)-imidazolidin-2-one hydrochloride m.p. 235° C. dec.; and 1-(1-azabicyclo[2.2.2]oct-3-yl)-3-(3-chloro-4-nitro-phenyl)-imidazolidin-2-one m.p. 155.5°–160.5° C.

EXAMPLE 4

Tablets each weighing 150 g and containing 60 mg of the active substance can be manufactured by blending and compressing the following ingredients:

| | |
|---|---|
| 1-(1-azabicyclo[2.2.2]oct-3-yl)-3-(3-chlorophenyl)-imidazolidin-2-one hydrochloride | 60 mg |
| Starch | 50 mg |
| Cellulose microcrystalline | 30 mg |
| Polyvinylpyrrolidone | 5 mg |
| Sodium carboxymethyl starch | 4.5 mg |
| Magnesium stearate | 0.5 mg |

EXAMPLE 5

Capsules, each dosed at 200 mg and containing 80 mg of the active substance can be prepared as follows:

| | |
|---|---|
| 1-(1-azabicyclo[2.2.2]oct-3-yl)-3-(3-chlorophenyl)-imidazolidin-2-one hydrochloride | 80 mg |
| Corn starch | 60 mg |
| Cellulose microcrystalline | 59 mg |
| Magnesium stearate | 1 mg |

This formulation can be encapsulated in two-piece hard gelatin capsules and dosed at 200 mg for each capsule.

We claim:

1. A compound of formula (I)

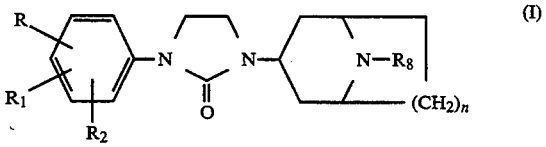

wherein
each of R, $R_1$, and $R_2$, which may be the same or different, is hydrogen, halogen, hydroxy, cyano, $C_1$–$C_6$ alkyl, $CF_3$, $CF_1$–$C_6$ alkoxy, $C_1$–$C_6$ alkylthio, formyl, $C_2$–$C_6$ alkanoyl, carboxy, $C_1$–$C_6$ alkoxycarbonyl, nitro, —$N(R_4R_5)$ in which each of $R_4$ and $R_5$ independently is hydrogen, $C_1$–$C_6$ alkyl, formyl or $C_2$–$C_6$ alkanoyl; or a $(R_6R_7)N$—$SO_2$ group, in which each of $R_6$ and $R_7$ independently is hydrogen or $C_1$–$C_6$ alkyl;

n is an integer of 1 or 2;

and $R_8$ is hydrogen, $C_1$–$C_6$ alkyl unsubstituted or substituted by phenyl, $C_2$–$C_4$ alkynyl, formyl or $C_2$–$C_6$ alkanoyl; or a pharmaceutically acceptable salt thereof.

2. A compound of claim 1, wherein each of R, $R_1$, and $R_2$, which may be the same or different, is hydrogen, halogen, cyano, $CF_3$, $C_1$–$C_4$ alklthio or $C_2$–$C_4$ alkoxy or —$N(R_4R_5)$ in which each of $R_4$ and $R_5$ independently is hydrogen, $C_1$–$C_4$ alkyl, formyl or $C_2$–$C_4$ alkanoyl; or a pharmaceutically acceptable salt thereof.

3. A pharmaceutical composition comprising a suitable carrier and/or diluent and, as a active principle, a compound of claim 1.

4. A compound selected from the group consisting of:
(endo)-1-(8-methyl-8-azabicyclo [3.2.1] oct-3-yl)-3-(3-chlorophenyl)-imidazolidin-2-one;
(exo)-1-(8-methyl-8-azabicyclo [3.2.1] oct-3-yl)-3-(3-chlorophenyl)-imidazolidin-2-one;
(endo)-1-(9-methyl-9-azabicyclo [3.3.1] non-3-yl)-3-(3-chlorophenyl)-imidazolidin-2-one;
(exo)-1-(9-methyl-9-azabicyclo [3.3.1] non-3-yl)-3-(3-chlorophenyl)-imidazolidin-2-one;
(endo)-1-(8-methyl-8-azabicyclo [3.2.1] oct-3-yl)-3-(5-chloro-2-methoxyphenyl)-imidazolidin-2-one;
(endo)-1-(9-methyl-9-azabicyclo [3.3.1] non-3-yl)-3-(5-chloro-2-methoxyphenyl)-imidazolidin-2-one;
or a pharmaceutically acceptable salt thereof.

* * * * *

UNITED STATES PATENT AND TRADEMARK OFFICE
CERTIFICATE OF CORRECTION

PATENT NO. : 5,401,750          Page 1 of 2
DATED : March 28, 1995
INVENTOR(S) : VARASI et al.

It is certified that error appears in the above-identified patent and that said Letters Patent is hereby corrected as shown below:

Column 2, line 51, delete "1-(1-azabicyclo[2.2.2]oct-3 yl)-3-(3-amino-4-chloro" and substitute therefor --1-(1-azabicyclo[2.2.2]oct-3 yl)-3-(4-amino-3-chloro--.

Column 8, line 62, delete "168°" and substitute therefor --163°--.

UNITED STATES PATENT AND TRADEMARK OFFICE
CERTIFICATE OF CORRECTION

PATENT NO. : 5,401,750
DATED : March 28, 1995
INVENTOR(S) : VARASI et al

It is certified that error appears in the above-indentified patent and that said Letters Patent is hereby corrected as shown below:

Column 10, line 12, delete "$CF_1$" and substitute therefor --$C_1$--;

line 21, after "phenyl," insert --$C_2$-$C_4$ alkenyl--.

Signed and Sealed this

Fourteenth Day of November, 1995

Attest:

BRUCE LEHMAN

*Attesting Officer*  *Commissioner of Patents and Trademarks*